United States Patent [19]

Hortmann et al.

[11] Patent Number: 4,611,598

[45] Date of Patent: Sep. 16, 1986

[54] MULTI-FREQUENCY TRANSMISSION SYSTEM FOR IMPLANTED HEARING AIDS

[75] Inventors: Guenter Hortmann, Neckartenzlingen; Klaus Kunick, Stuttgart, both of Fed. Rep. of Germany

[73] Assignee: Hortmann GmbH, Neckartenzlingen, Fed. Rep. of Germany

[21] Appl. No.: 726,222

[22] Filed: Apr. 22, 1985

[30] Foreign Application Priority Data

May 30, 1984 [DE] Fed. Rep. of Germany ....... 3420244

[51] Int. Cl.⁴ .......................... A61N 1/36; H04R 25/00
[52] U.S. Cl. .............................. 128/419 R; 179/107 R
[58] Field of Search ..................... 128/419 R, 421–422, 128/784–786; 179/107 R, 107 BC, 107 FD

[56] References Cited

U.S. PATENT DOCUMENTS

| 3,586,791 | 6/1971 | Puharich et al. | 179/107 R |
| 4,220,830 | 9/1980 | Schafer | 179/107 R |
| 4,400,590 | 8/1983 | Michelson | 179/107 FD |
| 4,419,995 | 12/1983 | Hochmair et al. | 128/419 R |
| 4,428,377 | 1/1984 | Zollner et al. | 128/419 R |
| 4,495,384 | 1/1985 | Scott et al. | 179/107 R |
| 4,515,158 | 5/1985 | Patrick et al. | 128/419 R |

FOREIGN PATENT DOCUMENTS

| 2811120 | 9/1978 | Fed. Rep. of Germany | 128/419 R |
| 2823798 | 9/1979 | Fed. Rep. of Germany | 128/419 R |

OTHER PUBLICATIONS

Merzenich et al., "Cochlear Implant Prostheses: Strategies and Progress" *Annals of Bio. Med. Eng.,* vol. 8, pp. 361–368, Jun. 5, 1981.
Hochmair et al, "An Implanted Auditory Eight Channel Stimulator for the Deaf" *Med. & Biol Eng. & Compat.,* vol. 19, No. 2, Mar. 1981, pp. 141–148.
Soma et al, "Fabrication and Packaging of an Implantable Multichannel Auditory Prosthesis" Conf. *IEEE 1980 Frontiers of Engineering in Health Care* Washington DC, Sep. 28–30, 1980, pp. 105–107.

*Primary Examiner*—William E. Kamm
*Assistant Examiner*—Mitchell J. Shein
*Attorney, Agent, or Firm*—Michael J. Striker

[57] ABSTRACT

A multi-frequency transmission system for implanted hearing aid includes an external transmitting part and an encapsuled receiver part implantable into middle ear of the user. The transmitting part includes a microphone, a speech processor including a set of audio frequency band pass filters connected respectively via adjustable threshold switches to pulse shapers which release an audio frequency band only when an adjusted threshold level is exceeded. A plurality of high frequency transmitters is modulated by the signals from the pulse shapers. A pair of additional high frequency transmitters is controlled by the pulses from the speech processor to alternately transmit high frequency pulses corresponding to the polarity of the triggering pulses. A frequency channel selector is connected between the transmitters and the speech processor to activate simultaneously one of the transmitters from the bipolar high frequency stage and one of the amplitude modulated transmitters. The combined signal is applied to a transmitting coil and received by a receiver unit implanted in user's ear. The receiver includes a plurality of resonant circuits assigned to respective high frequency transmitters and a pair of switching transistors of opposite type of conductivity which are power supplied by a portion of a rectified high frequency signal and control the polarity of the excitation signal applied to the implanted electrodes.

8 Claims, 6 Drawing Figures

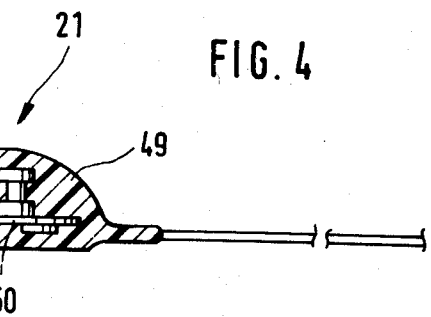
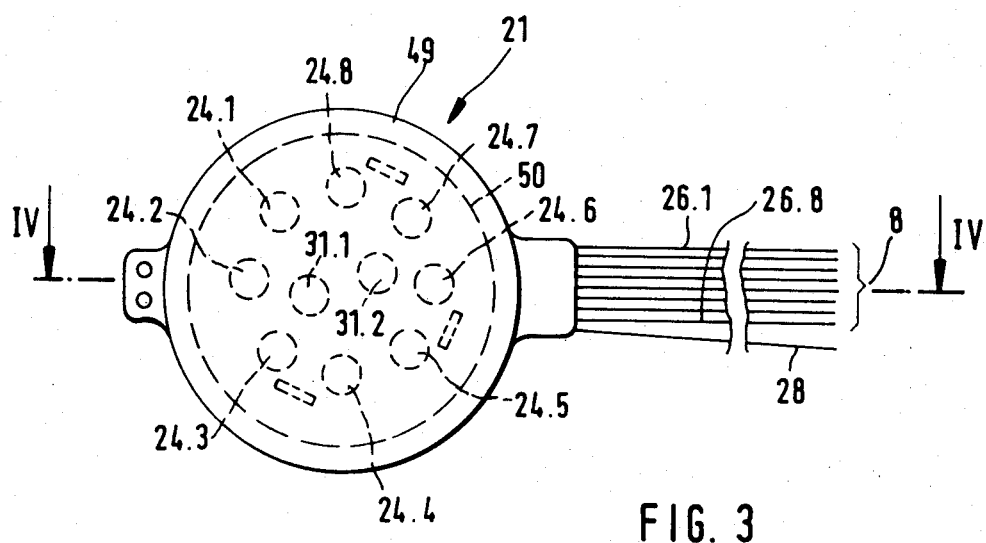

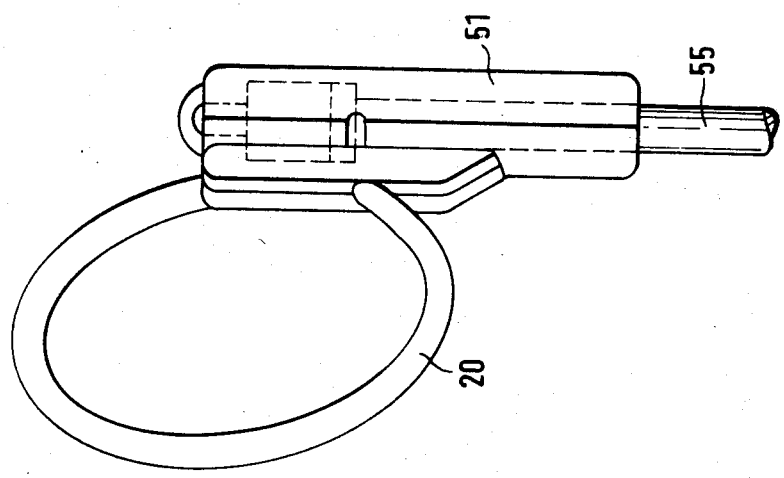
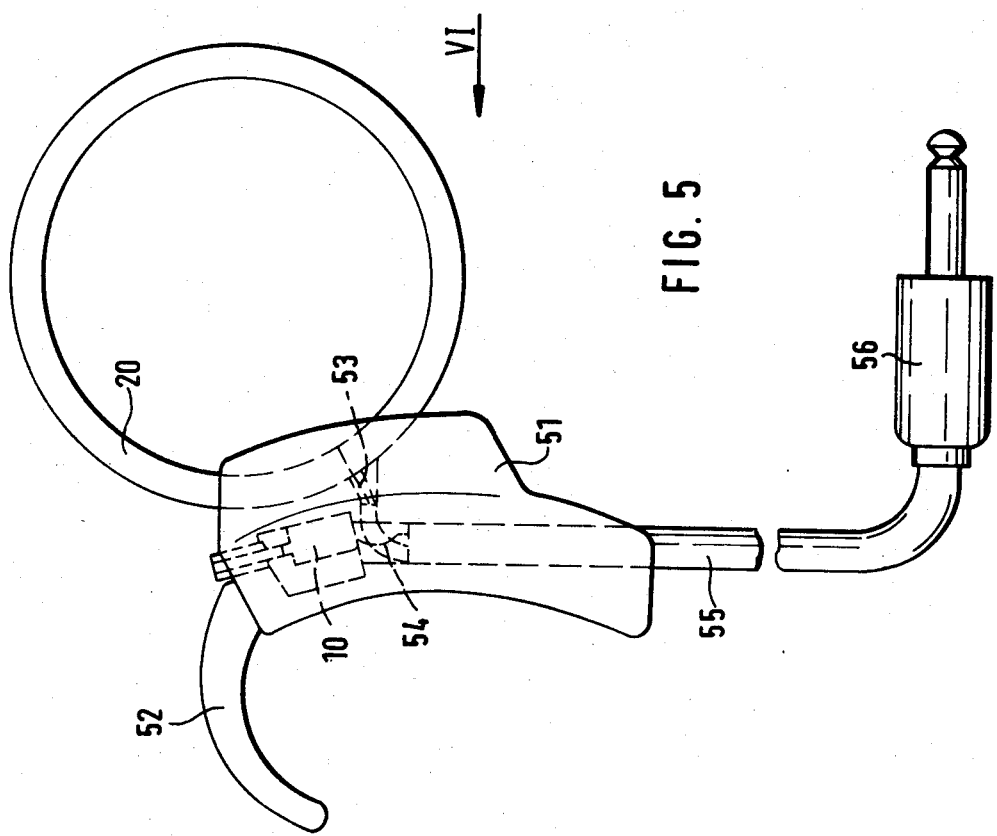

MULTI-FREQUENCY TRANSMISSION SYSTEM FOR IMPLANTED HEARING AIDS

BACKGROUND OF THE INVENTION

The present invention relates to a multi-frequency transmission system for implanted hearing aids of the type including a plurality of excitation electrodes implanted together with a receiving part in user's body; the transmitting part includes an electro-acoustic converter connected to a set of band pass filters for filtering a plurality of frequency bands in audio range, and a plurality of high frequency transmitters whose inputs are coupled to respective band pass filters so as to generate at their outputs an amplitude modulated high frequency carrier signal which is applied to a common transmitting coil. The implanted receiving parts have a single input channel and means for selectively applying the received audio frequency bands to the corresponding excitation electrodes.

It has been known how to electrically excite the inner ear of totally deaf persons whose auditory nerve is still intact, by means of a single excitation electrode or by a multiple electrode system which is inserted into the cochlea. The excitation electrodes are distributed on the latter and excited by a high frequency signal from an external receiver so that the auditory nerve of the patient provides an acoustic impression. The principal problem encountered in such prior art hearing aids is in producing such an excitation of the auditory nerve of the patient which would comply as close as possible with the natural hearing resulting from the acoustic conversion in the inner ear. The plural electrodes each vibrating at a different frequency range must be prevented from creating an overlap in the excitation which would make it impossible for the patient to distinguish the differences in received tones. Another problem encountered in implanted hearing aids is the necessity of a full implantation of the high frequency receiver in the patient's body inasmuch any outlets through the user's skin such as for example openings for the sockets of electrodes or other connecting components would require an artificial opening in the skin which of course would be exposed to the risk of an infection.

SUMMARY OF THE INVENTION

It is therefore a general object of the present invention to overcome the disadvantages of prior art hearing aids of this kind.

In particular, it is an object of this invention to provide a wireless multi-frequency transmission system for implanted hearing aids which are not possessed with the above described disadvantages.

Another object of this invention is to provide an implanted hearing aid which has an improved operational reliability and a better impression of a natural sound than the prior art insert receiver and hearing aid methods.

Still another object of this invention is to reduce the consumption of energy of the hearing aid.

In keeping with these objects and others which will become apparent here after, one feature of the invention resides in a combination in which the electro-acoustic converter is connected to a speech processor including the set of audio frequency band pass filters which are connected to the corresponding high frequency transmitters via threshold switches having adjustable threshold levels; the speech processor is connected to a bipolar transmitting stage including two additional high frequency transmitters which alternately generate pulses of the same length but of a different polarity; and a channel selection stage connected between the high frequency transmitters and the threshold switches in the speech processor to trigger simultaneously one of the high frequency transmitters and bipolar transmitting stage so that the latter and the selected transmitter apply to the transmitting coil a carrier signal modulated by one of the audio frequency band and by a pulse of one polarity. In the receiver there are also provided two additional frequency channels for receiving the alternating pulses from the high frequency transmitters in the bipolar transmitting stage. The whole transmission system may include for example ten transmission channels inclusive of the two additional channels for transmitting the pulses of alternating polarity.

The advantage of the wireless multi-frequency transmission system of this invention is the fact that the receiving part which is implantable into the patient's body, is constructed entirely of passive elements that means without any active power source. The excitation electrodes need not be inserted in the cochlea but can be implanted in the middle ear in the range of the promonotorium whereby the individual electrodes excite the audiotory nerve via bones. This novel arrangement is made possible due to the fact that this invention guarantees that an excitation electrode delivers a bipolar excitation pulse whereby the bipolarity of the pulse is controlled by the two additional high frequency transmitters in the bipolar stage at the transmitting part. The bipolarity of the excitation pulses is necessary for preventing electrolytical processes in the biological substrates or tissues in the ear. The switch over of the polarity of the received pulses is performed at the receiving part by means of switching transistors which are energized from the received signal without the need of a source of energy. The alternating pulses of opposite polarity transmitted from the bipolar stage are received in separate resonant circuits and the received signals are applied via resistors to the bases of two switching transistors of opposite types of conductivity. The pulse received at a resonant circuit is applied via a resistor to the base of a transistor of an assigned type of conductivity. The emitters of both transistors are connected to the mass and the collectors of the two switching transistors are power supplied from a rectified signal received at the resonant circuits assigned to respective high frequency transmission channels.

Another substantial advantage of the multi-frequency transmission system of this invention is to be seen in the fact that in order to minimize the energy consumption the receiving part includes resonants circuits for respective frequency channels whose impedance exceeds the load impedance of different excitation electrodes so that only minute currents flow through the respective resonant circuits. In the preferred embodiment of this invention, the transmitting coil is adjustably arranged on a holder which can be worn behind the ear in such a manner that the coil can be brought in a tight contact with the user's head exactly opposite the implanted receiving piece so that the transmission losses are reduced to a minimum.

The transmission system according to this invention provides reception of audio signals of proper quality and maximum reliability inasmuch the output impedance of individual frequency band channels and has the effect of excitation electrodes can be exactly matched to the sensitivity of the auditory nerve of a particular patient and also because there are always two electromagnetic high frequency fields carrying the corresponding audio frequencies with field strength sufficient for reliable excitation. In the transmitting part the output signals of individual frequency band channels are generated only in the case when the audio signal in the corresponding frequency range exceeds a minimum level. The generated high frequency carrier signal at the output of respective transmitters is modulated in a conventional manner by the amplitude of the signals from the threshold switches.

The novel features which are considered as characteristic for the invention are set forth in particular in the appended claims. The invention itself however both as to its construction and its method of operation, together with additional objects and advantages thereof, will be best understood from the following description of specific embodiments when read in connection with the accompanying drawing.

BRIEF DESCRIPTION OF THE DRAWING

FIG. 3 shows the implantable receiver unit with a set of excitation electrodes;

FIG. 4 is a sectional side view of the receiver unit taken along the line IV—IV in FIG. 3;

FIG. 5 is a side view of a holder for a transmitting coil; and

FIG. 6 is an elevation view of the holder for a transmitting coil viewed in the direction of arrow VI in FIG. 5.

DESCRIPTION OF THE PREFERRED EMBODIMENT

Figure 1:
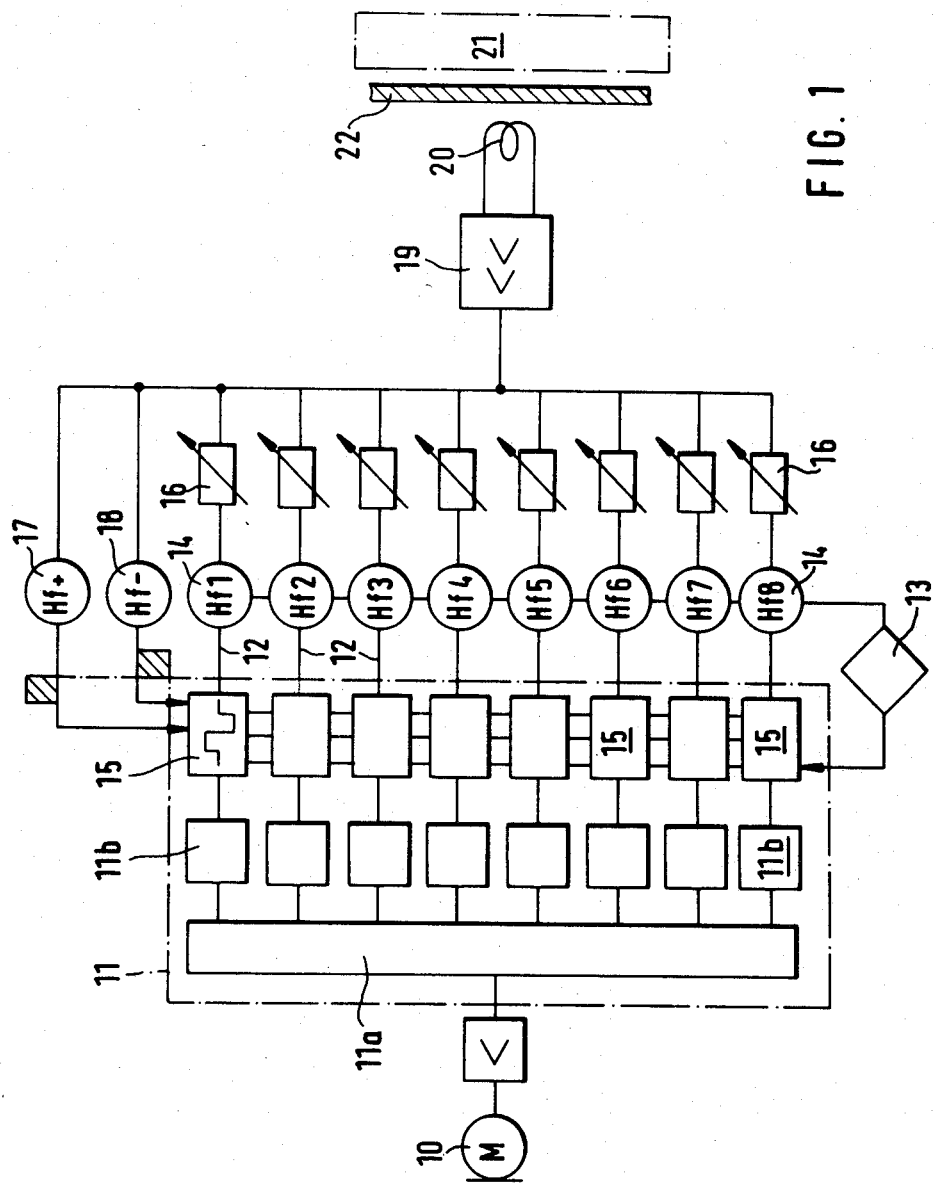
FIG. 1 is a functional block circuit diagram of the transmitting part and of the implanted receiving part of the transmission system of this invention.

Referring firstly to the schematic block circuit diagram in FIG. 1, the transmitting part of the transmission system of this invention includes an electro-acoustic convertor in the form of a microphone 10 which delivers analog audio signals to a speech processor 11. In the speech processor the electric audio signal is filtered in a set of band pass filters 11a which filter out eight audio frequency bands, for example. The speech processor 11 further includes a corresponding set of adjustable threshold switches 11b assigned to respective channels for the audio frequency bands. The threshold level of respective threshold switches is adjustable for example between 45 to 75 decibels. Only when the adjusted threshold level is exceeded the filtered output from the band pass filters can proceed via frequency channels 12 to a pulse shaping stage 15 which modulates the assigned high frequency transmitter 14. A frequency channel selecting stage 13 is coupled to the speech processor 11 in such a manner as to activate at a time only one of the pulse shapers 15. Each of the high frequency transmitters 14 delivers a carrier signal at a certain frequency which lies in the range between 1 to 5 megacycles. This carrier signal is modulated by the output from the pulse shaper 15. The output of each high frequency transmitter 14 is connected to a common point via a series connected potentiometer 16 which permits the adjustment of the transmitted amplitude of respective frequency channels so as to match these channels to different excitation sensitivities of the electrodes at the receiving side. A bipolar high frequency transmitting stage including additional high frequency transmitters 17 and 18 is connected between the common output point of the remaining transmitters 14 and the pulse shapers of the speech processor 11. The transmitters 17 and 18 are alternately triggered by successive pulses of opposite polarity. In this example, the high transmitter 17 is triggered by positive pulses and the transmitter 18 by negative pulses following in time one after the other and, for the sake of symmetry have the same length. As a consequence, the common output point of transmitters 14 and the common high frequency at stage 19 of the transmission system is supplied, in addition to the carrier signal, with signals delivered alternately by high frequency generators 17 and 18. The alternating signals from the latter generators are combined with the carrier signal from the selected transmitter 14 and applied to the transmitting coil 20 which is supported behind the ear of the patient. The signal from the coil propagates through the skin of the patient and is received by the resonant circuits in the implanted receiver unit 21.

Figure 2:
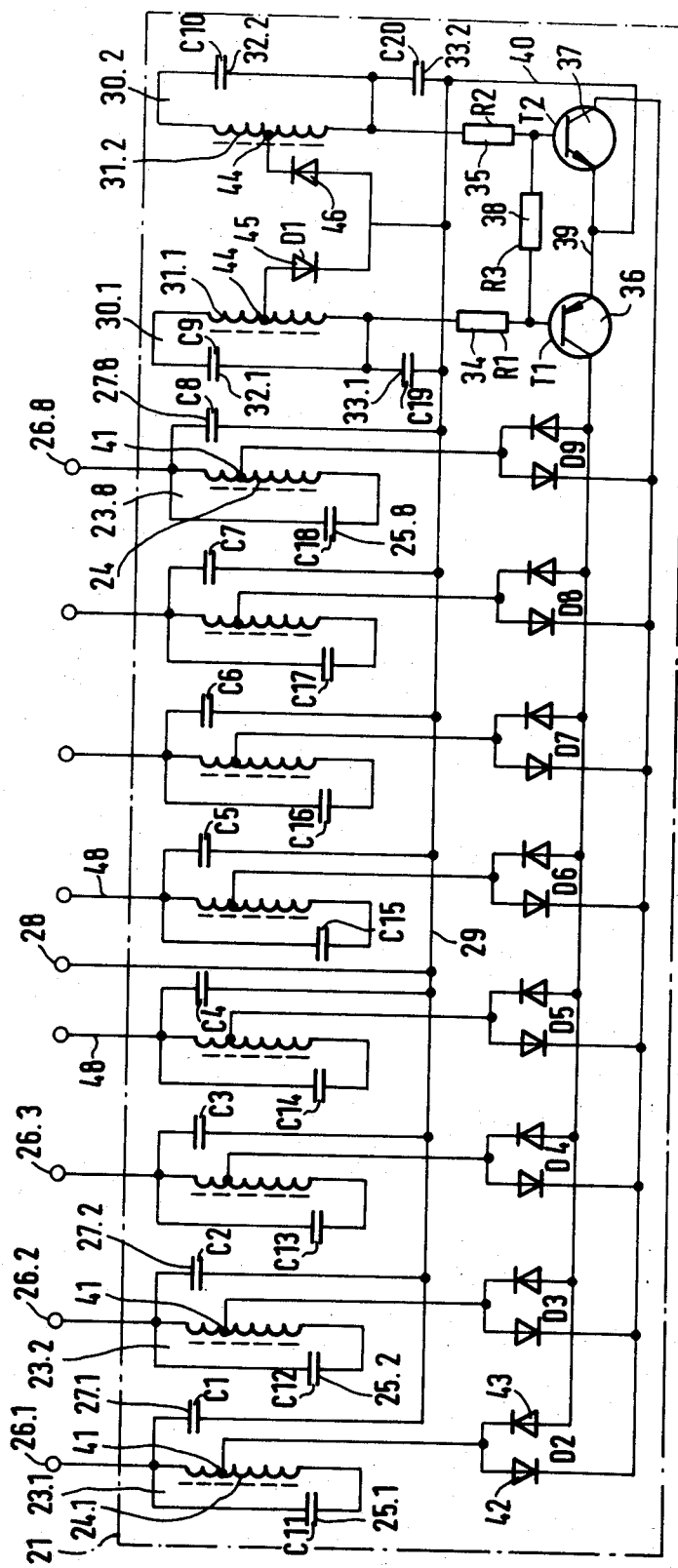
FIG. 2 shows a circuit diagram of the receiving part.

FIG. 2 illustrates the circuit of the implantable receiving unit 21. The receiver includes eight resonant circuits 23.1 to 23.8 tuned to frequency bands of respective transmission channels and consisting of a parallel connection of coils 24.1 through 24.8 with capacitors 25.1 through 25.8. Each resonant circuit is connected to terminals 26.1 through 26.8 leading to respective excitation electrodes and each resonant circuit is further connected via capacitors 27.1 through 27.8 and via a mass conduit 29 to a neutral or mass electrode 28.

Apart from the resonant circuits the receiver also includes two additional resonant circuits 30.1 and 30.2 for receiving pulsating signal components from the high frequency transmitters 17 and 18 of the bipolar transmitting stage. The additional resonant circuits include coils 31.1 and 31.2 connected in parallel with capacitors 32.1 and 32.2. The two additional resonant circuits are also connected via capacitors 33.1 and 33.2 to the common neutral electrode 28, and via resistors 34 and 35 to the bases of two switching transistors 36 and 37 of opposite types of conductivity. The bases of the two transistors are also interconnected by a coupling resistor 38 while the emitters of the two transistors are directly connected via a conduit 40 and the common or mass conduits 29 to the neutral electrode 28.

Each coil 24.1 through 24.8 is provided with a tapping point 41 which is connected via oppositely oriented rectifying diodes 42 and 43 to the collectors of the corresponding switching transistors 36 and 37 to energize the latter from the received high frequency signal.

By energizing the transistors from the tapping points 41 and 44 of the coils 24.1 through 24.8 and 31.1 and 31.2 it is achieved that the impedance of respective resonant circuits is larger than the impedance of the load and consequently that the oscillating currents in the circuits are small.

As mentioned before, the actuation of the high frequency tranmitters 14 at the transmitting part is controlled by pulses generated by the speech processor 11 and the channel selector 13. Simultaneously, depending on the polarity of the pulse generated by the speech processor one of the two additional high frequency transmitters 17 or 18 is actuated and the combined high frequency signal from one of the transmitters 14 and one of the transmitters 17 or 18 is transmitted via the transmitting coil and received in the receiver 21. Depending on the frequency of the received signal, one of the resonant circuits 30.1 or 30.2 is actuated and turns on the assigned switching transistors 36 or 37 which in turns applies a positive or negative bias to the amplitude modulated high frequency signals received by the receiver. If the control impulse from the pulse shaper in the speech processor 11 changes its polarity, then the actuation of the two additional transmitters 17 or 18 in the bipolar stage is also changed and the other additional high frequency transmitters is made active. Consequently, the opposite resonant circuit 30.1 or 30.2 at the receiving side is excited and turns over the polarity of the rectified voltage. This circuit construction guarantees a low consumption of energy and eliminates the use of active power supply elements at the implanted receiving unit.

FIGS. 3 and 4 illustrate the mechanical construction of the implantable receiver 21. A thin printed circuit board 50 supports at one side thereof the ten resonant circuits 24.1 through 24.8 and 31.1 and 31.2 which are arranged on a circular area of a diameter of about 25 millimeters. The remaining circuit components are located at the opposite side of the circular board and interconnected by thin copper conductors produced by an etching technique. To protect the receiver unit against penetration of liquid media from the patient's body, the entire circuit is embodied in a suitable plastic material which is compatible with the tissues of a human body. The protective plastic layer is indicated by reference numeral 49.

FIGS. 5 and 6 illustrate a hook-shaped holder 51 supporting the microphone 10 of the transmitting system. The microphone communicates with the outer surface of the holder through a non-illustrated sound receiving opening. The transmitting coil 20 is hinged to the holder 51 in such a manner as to enable its turning at an angle to the surface of the holder. For example, FIG. 6 shows the transmitting coil 20 forming an angle of about 30° to the plane of the holder 51. At the opposite side, the holder is provided with an adjustable yoke 52 which can be suspended on the ear of the patient whereby the holder 51 with the transmitting coil 20 tightly abuts against the skin of patient's head exactly opposite the implanted receiving part 21, namely opposite the receiving coils on the implanted board 50. A multiple core cable 55 is secured to the holder 51 and connects the core conduits 53 of the transmitting coil, and a core conduit 54 of the microphone with a plug 56 which is connectable into a separate unit housing the remaining components of the transmitting part of the multi-frequency transmission system of this invention. This (non-illustrated) transmitting unit can be carried by the patient at any suitable place. At the receiving side (FIG. 3) the terminals 26.1 through 26.8 as well as the neutral terminal 28 lead to non-illustrated excitation electrodes 8 which are also implanted in patient's body.

If desired, the holder 61 can support also other or all electronic components of the transmitting parts. The microphone 10 is located close to the point at which normally the ear receives sound waves. The pivotal attachment of the transmitting coil permits an individual adjustment of the position of the latter on the head of the patient so as to align the transmitted waves with the position of the implanted receiver unit 50.

It will be understood that each of the elements described above, or two or more together, may also find a useful application in other types of constructions differing from the types described above.

While the invention has been illustrated and described as embodied in a specific example of a transmission system for an implantable hearing aid, it is not intended to be limited to the details shown since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A multi-frequency transmission system of an implanted hearing aid, comprising
    means for converting an acoustic signal in an electric signal;
    a plurality of band pass filters connected to said converting means for filtering different frequency bands in audio frequency range;
    a plurality of high frequency transmitters each transmitting an amplitude modulated high frequency carrier signal;
    a speech processor including a plurality of threshold switching means connected respectively between said band pass filters and inputs of said high frequency transmitters, said threshold switching means having adjustable threshold levels;
    a bipolar transmitting stage including two additional high frequency transmitters connected to said speech processor to generate alternating high frequency pulses of the same length but of different polarity; said high frequency transmitters and said additional high frequency transmitters being connected via an end stage to a common transmitting coil;
    a channel selector connected between said high frequency transmitters and said threshold switching means to trigger simultaneously one of said high frequency transmitters and one of said additional high frequency transmitters in said bipolar transmitting stage; and
    receiving means implanted in user's body, said receiving means including a single high frequency input channel and a plurality of excitation electrodes responsive to different frequencies of the received signal.

2. A multi-frequency transmission system as defined in claim 1, wherein said receiving means includes a plurality of resonant circuits for receiving carrier frequencies of respective high frequency transmitters and the frequencies of respective additional high frequency transmitters of the bipolar transmitting stage, means for connecting the resonant circuits to the assigned excitation electrodes whereby the impedance of the resonant circuits exceeds the impedance of said electrodes.

3. A multi-frequency transmission system as defined in claim 2, further comprising two switching transistors of a different type of conductivity, said means for connecting the resonant circuits to the excitation electrodes including a common point coupled to respective resonant circuits and to the emitters of said switching transistors, the bases of said transistors being connected to the resonant circuits for receiving the high frequency pulses from said bipolar transmitting stage, and the collectors of said switching transistors being coupled via oppositely polarized pairs of rectifying elements to the resonant circuits for receiving the carrier signals, and the resonant circuits for receiving the high frequency pulses from said bipolar transmitting stage being coupled via oppositely polarized rectifiers to said common point.

4. A multi-frequency transmission system as defined in claim 3, wherein the carrier frequency bands are withing the range of 1 to 5 megacycles.

5. A multi-frequency transmission system as defined in claim 4, wherein said receiving means includes ten resonant circuits supported together with terminals for the excitation electrodes on a board having a maximum diameter of 25 millimeters.

6. A multi-frequency transmission system as defined in claim 5, wherein said transmitting coil and said converting means are mounted on a holder, said holder being provided with an adjustable yoke for the attachment to the user's ear are whereby the transmitting coil is brought in close contact with the user's skin opposite the implanted receiving board.

7. A multi-frequency transmission system as defined in claim 6, wherein said transmitting coil is swingably mounted on said holder to facilitate the adjustment of the position of the coil relative to the user's body.

8. A multi-frequency transmission system as defined in claim 7, wherein said converting means and said transmitting coil are electrically connected via a multi-core cable to a unit housing the remaining components of the transmitting part of the system.

* * * * *